United States Patent
Ogata et al.

(10) Patent No.: US 6,288,056 B1
(45) Date of Patent: Sep. 11, 2001

(54) INTERMITTENT CLAUDICATION THERAPEUTIC DRUGS COMPRISING PYRROLOAZEPINES

(75) Inventors: Atsuto Ogata, Osaka; Norio Inomata, Mino; Akira Mizuno, Kyoto, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/673,514

(22) PCT Filed: Feb. 17, 2000

(86) PCT No.: PCT/JP00/00883

§ 371 Date: Oct. 17, 2000

§ 102(e) Date: Oct. 17, 2000

(87) PCT Pub. No.: WO00/48602

PCT Pub. Date: Aug. 24, 2000

(30) Foreign Application Priority Data

Feb. 17, 1999 (JP) .................................................. 11-038631

(51) Int. Cl.$^7$ .................................................. A61K 31/55
(52) U.S. Cl. .................................................. 514/211.05
(58) Field of Search ........................................ 514/211.05

(56) References Cited

FOREIGN PATENT DOCUMENTS 0 807 632 * 12/1996 (EP) .

OTHER PUBLICATIONS

Patent Abstracts of Japan, vol. 017, No. 309, Jun. 14, 1993, JP 05–025128, Feb. 2, 1993.

* cited by examiner

Primary Examiner—Raymond Henley, III
(74) Attorney, Agent, or Firm—Oblon, Spivak, McClelland, Maier & Neustadt, P.C.

(57) ABSTRACT

A method of treating or improving intermittent claudication, which comprises administering, to a patient with intermittent claudication, a pyrroloazepine derivative or a pharmacologically acceptable salt thereof, said pyrroloazepine derivative being represented by the following formula (I):

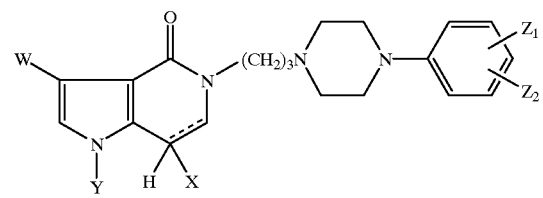

(I)

wherein the dotted line indicates existence or nonexistence of a bond; when the bond of the dotted line exists, X does not exist, and, when the bond of the dotted line does not exist, X represents a hydrogen atom, a hydroxy group or a group $OR_1$ in which $R_1$ represents a substituted or unsubstituted alkyl group; Y represents a linear or branched, substituted or unsubstituted alkyl group; $Z_1$ and $Z_2$ are the same or different and each independently represent a hydrogen atom, a hydroxy group or a halogen atom; and W represents a hydrogen atom or a methyl group.

6 Claims, No Drawings

INTERMITTENT CLAUDICATION THERAPEUTIC DRUGS COMPRISING PYRROLOAZEPINES

This is a 371 of PCT/JP00/00883 filed Feb. 17, 2000.

TECHNICAL FIELD

This invention relates to intermittent claudication therapeutic drugs which comprise pyrroloazepine derivatives as active ingredients. More specifically, this invention is concerned with intermittent claudication therapeutic drugs which comprise as active ingredients pyrrolo[3,2-c]azepine derivatives or pharmacologically acceptable salts thereof and which further prevent or improve chronic arterial occlusive diseases, arteriosclerosis obliterans and thromboangiitis obliterans.

BACKGROUND ART

Chronic arterial occlusive diseases indicate diseases characterized by peripheral blood flow disturbances and are represented by arteriosclerosis obliterans and thromboangiitis obliterans. For symptoms of blood flow disturbances, the Fontaine's classification is applied to determine their severity of the diseases and treatment methods. According to this classification, they are divided into stage I: rhigosis or numbness at legs, stage II: intermittent claudication, stage III: rest pain, and stage IV: ulceration. At present, many patients complain of intermittent claudication, and the number of patients is increasing year after year.

Intermittent claudication is a symptom common to chronic arterial occlusive diseases, especially to arteriosclerosis obliterans or thromboangiitis obliterans, all of which are associated primarily with chronic obstructions of large arteries of legs, and means a state in which upon muscle work, ischemia of leg muscles occurs and continuation of walking becomes difficult due to a dull pain, numbness or the like caused by the muscle ischemia, but a rest makes it possible to resume walking. It is considered to be a main cause that at a hypertrophic part of a tunica intima resulted from arteriosclerosis of a large artery in a leg, a thrombus is formed with expulsion of the tunica intima, hemorrhage, ulceration of the tunica intima or the like as an impetus, leading to obstruction of a lumen, and an ischemic disturbance occurs at a periphery of the large artery [Itoh, M., et al., Geriatric Medicine, 33, 857–880 (1995)].

In a patient with intermittent claudication, vascular endothelial cells have been damaged by arteriosclerosis, or often by his additional diseases such as hypertension, hyperlipidemia or diabetes. Adhering and aggregating ability for platelets has therefore been potentiated at the damaged site, and as a result of platelet aggregation, various vasoconstrictors containing serotonin are released, leading to further potentiation of vasoconstriction. There is hence an outstanding demand for drug capable of inhibiting both platelet aggregation and vasoconstriction at the same time and moreover, of acting specifically to the site of a lesion, especially having a potency profile particularly suited for the improvement of intermittent claudication.

In recent years, some compounds have been disclosed as potent therapeutic drugs for intermittent claudication. However, none of them are satisfactory in potency, effective duration, toxicity and side effects, or such potency profile as mentioned above.

As is appreciated from the foregoing, it is the current circumstance that practically no suitable drug is available for the treatment or improvement of intermittent claudication, and development of drug having high effectiveness is desired [William, R. H., Vascular Medicine, 2. 257–262 (1997)].

Accordingly, an object of the present invention is to provide a drug for treating or improving intermittent claudication, which can satisfy characters in potency, effect duration, toxicity and side effects, and potency profile. Another object of the present invention is to provide a preventive or therapeutic drug for chronic arterial occlusive diseases, arteriosclerosis obliterans or thromboangiitis obliterans.

DISCLOSURE OF THE INVENTION

With the foregoing circumstances in view, the present inventors have proceeded with extensive research, seeking for compounds which have strong action and long effect duration, exhibit stable action for a long time, have low toxicity and side effects, and possess a potency profile best suited for the treatment and improvement of intermittent claudication. As a result of evaluation of drug efficacy and toxicity and evaluation of side effects by various in vivo evaluation models, the present invention has been completed based on finding that strong serotonin (5-$HT_2$) receptor blocking action and mild adrenargic ($\alpha_1$) receptor blocking action—which pyrroloazepine derivatives represented by the following formula (I):

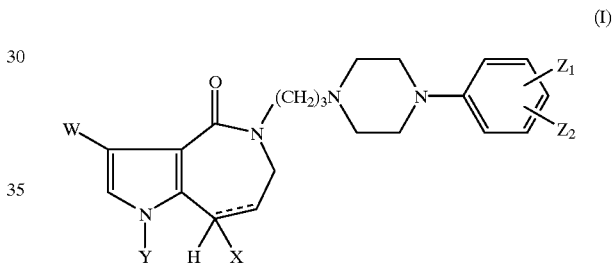

wherein the dotted line indicates existence or non-existence of a bond; when the bond of the dotted line exists, X does not exist, and, when the bond of the dotted line does not exist, X represents a hydrogen atom, a hydroxy group or a group $OR_1$ in which $R_1$ represents a substituted or unsubstituted alkyl group; Y represents a linear or branched, substituted or unsubstituted alkyl group; $Z_1$ and $Z_2$ are the same or different and each independently represent a hydrogen atom, a hydroxy group or a halogen atom; and W represents a hydrogen atom or a methyl group—surprisingly provide well-balanced inhibitory actions against platelet aggregation and lesion-specific vasoconstriction and have a potency profile optimal as long-awaited intermittent claudication therapeutic drugs.

Therefore, the present invention provides a therapeutic drug for intermittent claudication, which comprises as an active ingredient a pyrroloazepine derivative represented by the formula (I) or a pharmacologically acceptable salt thereof, and hence provides a preventive or therapeutic for chronic arterial occlusive diseases, a preventive or therapeutic for arteriosclerosis obliterans, and a preventive or therapeutic for thromboangiitis obliterans, all of which comprise as an active ingredient a pyrroloazepine derivative represented by the formula (I) or a pharmacologically acceptable salt thereof. The active ingredient has excellent properties as a medicament, including extremely strong action, long effect duration and superb oral absorption, and moreover specifically inhibits vasoconstriction at the site of a lesion. These preventing and therapeutic drugs, therefore, have marked characteristics that they advantageously act for the enhancement of blood flow not only at peripheral area but also at proximal area without developing hypotension or a headache which would otherwise occur due to nonspecific vasodilating action. In addition, concerning action on blood vessels themselves, they effectively act mainly at the area, where a damage was received and a lesion has advanced, not only on arteries but also on veins and thus inhibit platelet aggregation.

The present invention also provide a method of treating or improving intermittent claudication, which comprises administering to a patient with intermittent claudication a pyrroloazepine derivative represented by the formula (I) or a pharmacologically acceptable salt thereof; and also use of a pyrroloazepine derivative represented by the formula (I) or a pharmacologically acceptable salt thereof for the production of an intermittent claudication therapeutic drug.

BEST MODES FOR CARRYING OUT THE INVENTION

The pyrroloazepine derivative (I) as the active ingredient in the intermittent claudication therapeutic drug according to the present invention is an already known compound or a compound producible in accordance with a known process.

Specifically, such pyrroloazepine derivatives are disclosed in PCT International Publication No. WO97/20845 filed by the present Applicant, and can be produced following the description of the PCT international publication.

As preferred examples of the group X in the pyrroloazepine derivative (I), the group X may not exist when the bond of the dotted line exists, and the group X may be a hydroxy group, a hydrogen atom or a group $OR_1$ when the bond of the dotted line does not exist. Among such pyrroloazepine derivatives, those without the optional double bond of the dotted line and containing a hydrogen atom as W and a hydroxy group as the group X are particularly preferred.

Preferred examples of $R_1$ in the group $OR_1$ can include linear or branched alkyl groups having 1 to 4 carbon atoms preferably, such as methyl and ethyl. One or more hydrogen atoms in each of these groups may be substituted by halogen atom(s) such as fluorine atom(s), chlorine atom(s) or bromine atom(s) or by alkoxy group(s) having 1 to 4 carbon atoms preferably, such as methoxy group(s) or ethoxy group (s). Methyl can be mentioned as a particularly preferred example of the group $R_1$.

Preferred examples of the group Y, which is bonded to the nitrogen atom of the pyrrole ring, can include linear or branched alkyl groups having 1 to 6 carbon atoms preferably, such as methyl, ethyl, n-propyl and isopropyl. One or more hydrogen atoms in each of these groups may be substituted by halogen atom(s) such as fluorine atom(s), chlorine atom(s) or bromine atom(s) or by alkoxy group(s) having 1 to 4 carbon atoms preferably, such as methoxy group(s) or ethoxy group(s). Methyl can be mentioned as a particularly preferred example of the group $R_1$.

The groups $Z_1,Z_2$ on the benzene ring may be the same or different, and each independently represent a hydrogen atom, a hydroxy group, or a halogen atom such as fluorine, chlorine or bromine. Combinations of a hydrogen atom as $Z_1$ and a hydrogen atom, a hydroxyl group or a halogen atom as $Z_2$ are preferred, and combinations of a hydrogen atom as $Z_1$ and a hydrogen atom, a hydroxyl group or a fluorine atom as $Z_2$ are particularly preferred. Of these, the combination of a hydrogen atom as $Z_1$ and a fluorine atom bonded to the p-position as $Z_2$ is most preferred. Further, W represents a hydrogen atom or a methyl group, with a hydrogen atom being particularly preferred.

Among these pyrroloazepine derivatives of the formula (I), the most preferred one is (±)-5-[3-[4-(4-fluorophenyl) piperazin-1-yl]propyl]-8-hydroxy-1-methyl-1,4,5,6,7,8-hexahydropyrrolo[3,2-c]azepin-4-one or (−)-(S)-5-[3-[4-(4-fluorophenyl)piperazin-1-yl]propyl]-8-hydroxy-1-methyl-1, 4,5,6,7,8-hexahydropyrrolo[3,2-c]azepin-4-one.

In addition to the pyrroloazepine derivatives of the formula (I), their pharmacologically acceptable salts can also be used in the present invention. Illustrative of acids applicable for the conversion into such salts are inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid. Further, the pyrroloazepine derivatives (I) and pharmacologically acceptable salts thereof in the present invention may be provided in the form of solvates.

To treat or improve intermittent claudication with the pyrroloazepine derivative of the formula (I) in the present invention, it is administered generally as a pharmaceutical preparation in desired one of various preparation forms by using a known manufacturing technique although it can be administered by itself in an effective amount.

Examples of an administration route for the drug of the present invention can include oral administration making use of tablets, powder, granules, capsules or syrups; and parenteral administration relying upon injections or suppositories. In view of readiness in administration, oral administration is preferable, and as a matter of fact, oral administration can bring about sufficient effects.

Upon formulation of the above-described pharmaceutical preparations, pharmaceutically acceptable diluents or carriers in the form of aqueous or oily liquids or solids can be used. Examples of such diluents or carriers can include polyvinylpyrrolidone, gum arabic, gelatin, sorbitol, cyclodextrin, tragacanth gum, magnesium stearate, talc, polyethylene glycol, polyvinyl alcohol, silica, lactose, crystalline cellulose, sucrose, starch, calcium phosphate, vegetable oil, carboxymethylcellulose, sodium laurylsulfate, purified water, ethanol, glycerin, and mannitol.

The intermittent claudication therapeutic drug, which comprises the pyrroloazepine of the formula (I) as an active ingredient, can be administered to patients complaining intermittent claudication or to patients who are likely to develop intermittent claudication. Illustrative of the patients, who are complaining intermittent claudication, are patients with peripheral circulatory disturbances and patients suffering from chronic arterial occlusive disease, for example, arteriosclerosis obliterans or thromboangiitis obliterans. The intermittent claudication therapeutic drug can be used to prevent or treat such diseases.

The dosage of the intermittent claudication therapeutic drug according to the present invention varies depending on the administration route and the age, body weight, conditions, etc. of the subject to be administered. In oral administration, a daily dosage may generally range from about 1 mg to 1,000 mg in terms of the pyrroloazepine derivative of the formula (I).

The present invention will next be described in further detail by the following preparation examples and tests. It is however to be noted that the present invention is by no means limited to or by the following examples.

Preparation Example 1
Synthesis of Ethyl 1-methyl-3-pyrrolecarboxylate (Compound 1)

After a mixture of N-formylsarcosine (117.1 g, 1 mole), ethyl propiolate (98.1 g, 1 mole) and acetic anhydride (638 ml) was stirred for 22 hours over an oil bath of 130° C., the reaction mixture was concentrated under reduced pressure.

Toluene (100 ml) was added to the residue, followed by concentration under reduced pressure. These procedures were repeated again, and the resulting brown oil was distilled under reduced pressure. A fraction was collected at 103 to 104° C. under 4 mmHg, whereby the title compound (109.19 g) was obtained (yield: 71.3%).

Preparation Example 2
Synthesis of 1-methyl-3-pyrrolecarboxylic Acid (Compound 2)

A mixture of Compound 1 (7.66 g, 50 mmole), which had been obtained in Preparation Example 1, and a 2 N aqueous solution of sodium hydroxide (37.5 ml, 75 mmole) was refluxed for 2 hours. The reaction mixture was cooled to 0° C., to which 6 N hydrochloric acid was added under stirring to acidify the same. Sodium chloride (15 g) was then added, followed by stirring for 1 hour over an ice-acetone bath. Precipitated crystals were collected. Those crystals were washed with chilled water and then dried under reduced pressure, whereby the title compound (5.77 g) was obtained (yield: 92.2%).

Preparation Example 3
Synthesis of Benzyl 3-(1-methyl-3-pyrrolecarboxamido)propionate (Compound 3)

To a solution of Compound 2 (5.01 g, 40 mmole) and benzyl β-alanine ester p-toluenesulfonate (16.87 g, 48 mmole) in N,N-dimethylformamide (hereinafter called "DMF") (200 ml), a solution of diethyl phosphorocyanidate (7.83 g, 48 mmole) in DMF (50 ml) was added dropwise under ice-cooling and stirring. A solution of triethylamine (9.71 g, 96 mmole) in DMF (50 ml) was then added dropwise, and the reaction mixture was stirred at room temperature for 67 hours.

The reaction mixture was concentrated under reduced pressure, followed by the addition of ethyl acetate-benzene (3:1 v/v) to the residue. The resulting mixture was washed successively with a half-saturated aqueous solution of potassium carbonate, water, a 10% aqueous solution of citric acid, water and a saturated aqueous solution of sodium chloride (hereinafter called "saturated brine"), dried over anhydrous sodium sulfate, and then concentrated under reduced pressure. The residue was washed with hexane and then recrystallized from ethyl acetate-hexane, whereby the title compound (9.44 g) was obtained (yield: 82%).

Preparation Example 4
Synthesis of 3-(1-methyl-3-pyrrolecarboxamido)propionic Acid (Compound 4)

5%-palladium/carbon (716 mg) was added to a solution of Compound 3 (7.16 g, 25 mmole) in tetrahydrofuran (hereinafter called "THF") (300 ml), followed by stirring for 72 hours under a hydrogen gas stream. The reaction mixture was filtered, and the solid was washed with methanol. The filtrate and the washing were combined, followed by concentration under reduced pressure. The residue was recrystallized from acetonitrile, whereby the title compound (4.14 g) was obtained (yield: 84%).

Preparation Example 5
Synthesis of 1-methyl-1,4,5,6,7,8-hexahydropyrrolo[3,2-c]azepine-4,8-dione (Compound 5)

A mixture of Compound 4 (348 mg, 1.5 mmole) and polyphosphoric acid (80%, 17.5 g) was stirred at 100° C. for 1 hour. Water (150 ml) was added to the reaction mixture, followed by the addition of potassium carbonate to adjust the pH to 5. The resulting mixture was saturated with sodium chloride and then extracted with THF (3 times). The organic layers were combined, washed with saturated brine, dried over anhydrous sodium sulfate, and then concentrated under reduced pressure. The residue was fractionated and purified by chromatography on a silica gel column (eluent: 3%-methanol/chloroform), whereby Compound 5 (161 mg) was obtained (yield: 50%).

Preparation Example 6
Synthesis of 5-(3-chloropropyl)-1-methyl-1,4,5,6,7,8-hexahydropyrrolo[3,2-c]azepine-4,8-dione (Compound 6)

To a solution of potassium t-butoxide (1.68 g, 15 mmole) in THF (40 ml), Compound 5 (1.34 g, 7.5 mmole) was added under ice-cooling and stirring. After the reaction mixture was stirred at 0° C. for 1 hour, a solution of 1-bromo-3-chloropropane (5.90 g, 37.5 mmole) in THF (40 ml) was added dropwise at the same temperature. The resulting mixture was then stirred at room temperature for 93 hours.

An aqueous solution of citric acid monohydrate (1.58 g) was added to the reaction mixture, followed by concentration under reduced pressure. Water was added to the residue, and the resulting mixture was extracted with chloroform (twice). The organic layers were combined, washed with saturated brine, dried over anhydrous sodium sulfate, and then concentrated under reduced pressure. The residue was purified by chromatography on a silica gel column (eluent: ethyl acetate:hexane=2:1), whereby the title compound (628 mg) was obtained (yield: 33%).

Preparation Example 7
Synthesis of 5-(3-chloropropyl)-1-methyl-1,4,5,6,7,8-hexahydropyrrolo[3,2-c]azepine-4,8-dione (Compound 6) (Alternative Process)

(i) Synthesis of Ethyl 3-[1-methyl-3-[N-(3-chloropropyl)]pyrrolecarboxamido]propionate (Compound 7)

A suspension of Compound 2 (50.05 g, 400 mmole) in THF (180 ml) was cooled to −5° C., to which a solution of oxalyl chloride (50.77 g, 400 mmole) in THF (20 ml) was added under stirring over about 5 minutes, followed by the addition of DMF (200 μl). After the reaction mixture was stirred at room temperature for 1.5 hours, THF (200 ml) and ethyl 3-(3-chloropropyl)aminopropionate hydrochloride (101.3 g, 400 mmole) were added successively. The reaction mixture was cooled to −5° C., to which a solution of triethylamine (161.9 g, 1.60 mole) in THF (200 ml) was added dropwise under stirring at such a rate that the internal temperature did not exceed 10° C. The resulting mixture was stirred under ice cooling for 10 minutes and then at room temperature for 1.5 hours.

Ethyl acetate was added to the reaction mixture. The organic layer was washed successively with 1/3 saturated brine, 2 N hydrochloric acid, 1/3 saturated brine, saturated aqueous solution of sodium hydrogen-carbonate-saturated brine (2:1 v/v), and saturated brine, dried over anhydrous sodium sulfate and then concentrated under reduced pressure, whereby a crude product (120.22 g) was obtained.

Although this material was substantially pure, a portion of the same was purified by chromatography on a silica gel column (eluent: 2%-methanol/chloroform), and its physical property data were measured. As a result, it was confirmed to be the title compound.

(ii) Synthesis of 3-[1-methyl-3-[N-(3-chloropropyl)] pyrrolecarboxamido]propionic Acid (Compound 8)

To a solution of the crude product (118.81 g), which had been obtained above in the synthesis (i), in THF (47.4 ml), a 2 N aqueous solution of sodium hydroxide (237 ml, 474 mmole) which had been chilled in advance was added dropwise under ice-cooling and stirring at a rate such that the internal temperature did not exceed 5° C. The reaction mixture was stirred at room temperature for 30 minutes.

The reaction mixture was ice-cooled and then washed with toluene. After 6 N hydrochloric acid (79 ml) was added to the water layer under ice-cooling and stirring at a rate such that the internal temperature did not exceed 50° C., the resulting mixture was extracted with dichloromethane (twice). The dichloromethane layers were combined, washed with water and saturated brine, dried over anhydrous sodium sulfate, and then concentrated under reduced pressure, whereby a crude product (108.05 g) was obtained.

Although this material was substantially pure, a portion of the same was purified by chromatography on a silica gel column (eluent: 10%-methanol/chloroform), and its physical property data were measured. As a result, it was confirmed to be the title compound.

(iii) Synthesis of 3-[1-methyl-3-[N-(3-chloropropyl)] pyrrolecarboxamido]propionic Acid Dicyclohexylamine Salt (Compound 9)

To a solution of the crude product (106.68 g), which had been obtained above in the synthesis (ii), in ethyl acetate (390 ml), dicyclohexylamine (70.71 g, 390 mmole) was added dropwise under ice-cooling and stirring. After the reaction mixture was stirred under ice-cooling for 30 minutes and then at room temperature for 16 hours, precipitated crystals were collected by filtration and dried under reduced pressure, whereby the title compound (136.17 g) was obtained (overall yield from 1-methyl-3-pyrrolecarboxylic acid: 77%).

(iv) Synthesis of 5-(3-chloropropyl)-1-methyl-1,4,5,6,7,8-hexahydropyrrolo[3,2-c]azepine-4,8-dione (Compound 6)

A mixture of phosphorus pentoxide (494 mg, 3.48 mmole) and methanesulfonic acid (3.00 g, 31.2 mmole) was stirred at 90° C. until it became homogeneous, and was then ice-cooled. To the resulting mixture, Compound 9 (1.36 g, 3 mmole) was added under stirring, followed by heating and stirring at 90° C. for 30 minutes. The reaction mixture was ice-cooled. Subsequent to addition of ice water (16 g), the resulting mixture was extracted three times with chloroform. The chloroform layers were combined, washed with water and saturated brine, dried over anhydrous sodium sulfate, and then concentrated under reduced pressure. The residue was isolated and purified by chromatography on a silica gel column (eluent: 1%-methanol/chloroform), whereby Compound 6 (635 mg) was obtained (yield: 83%).

EXAMPLE 8

Synthesis of 5-[3-[4-(4-fluorophenyl)piperazin-1-yl]propyl]-1-methyl-1,4,5,6,7,8-hexahydropyrrolo[3,2-c]azepine-4,8-dione (Compound 10)

A suspension of Compound 6 (611 mg, 2.4 mmole), 1-(4-fluorophenyl)piperazine (649 mg, 3.6 mmole), potassium carbonate (498 mg, 3.6 mmole) and sodium iodide (720 mg, 4.8 mmole) in acetonitrile (30 ml) was refluxed for 38 hours.

The reaction mixture was concentrated under reduced pressure, followed by the addition of a half-saturated aqueous solution of potassium carbonate to the residue. The resulting mixture was extracted with chloroform (twice). The organic layers were combined, washed with saturated brine, dried over anhydrous sodium sulfate, and then concentrated under reduced pressure. The residue was purified by chromatography on a silica gel column (eluent: 10%-methanol/ethyl acetate), whereby the title compound (1.02 g) was obtained (yield: 99%).

Preparation Example 9

Synthesis of (±)-5-[3-[4-(4-fluorophenyl)piperazin-1-yl]propyl]-8-hydroxy-1-methyl-1,4,5,6,7,8-hexahydropyrrolo[3,2-c]azepin-4-one (Compound 11)

To a solution of Compound 10 (797 mg, 2 mmole) in ethanol (30 ml), sodium borohydride (757 mg, 20 mmole) was added in small portions under ice-cooling and stirring. The reaction mixture was stirred at 0° C. for 30 minutes and then at room temperature for 16 hours.

Water was added to the reaction mixture, and the resulting mixture was stirred at room temperature for 1 hour and then concentrated under reduced pressure. Water was added to the residue, followed by extraction with chloroform. The organic layer was washed with saturated brine, dried over anhydrous sodium sulfate, and then concentrated under reduced pressure. The residue was purified by chromatography on a silica gel column (eluent: 20%-methanol/ethyl acetate), whereby the title compound (710 mg) was obtained (yield: 89%).

IR (KBr/cm$^{-1}$): 3258, 2820, 1595, 1509, 1482, 1432, 1378, 1287, 1220, 1162, 1027, 952, 926, 832, 742, 674.

NMR (measured in CDCl$_3$, using TMS as an internal standard, 400 MHz, δ ppm): 1.82 (2H,quint,J=7.3 Hz), 2.15–2.32 (3H,m), 2.44 (2H,t,J=7.3 Hz), 2.60 (4H,m), 3.11 (4H,m), 3.34 (1H,m), 3.52 (1H,m), 3.59–3.70 (2H,m), 3.72 (3H,s), 4.91 (1H,br.s), 6.61 (1H,d,J=2.9 Hz), 6.70 (1H,d,J=2.9 Hz), 6.87 (2H,m), 6.95 (2H,m).

Preparation Example 10

Optical Resolution of (±)-5-[3-[4-(4-fluorophenyl)piperazin-1-yl]propyl]-8-hydroxy-1-methyl-1,4,5,6,7,8-hexahydropyrrolo[3,2-c]azepin-4-one (Compound 11) by a Chiral Acid (Synthesis of the (−)-(S) Isomer of Compound 11)

Compound 11 (20.0 g, 50 mmole) was dissolved under heat in methanol (160 ml). After cooling, L-(+)-tartaric acid (7.50 g, 50 mmole) was added. The resulting mixture was seeded, followed by stirring at room temperature for 24 hours. Precipitated crystals were collected by filtration. Colorless crystals (11.8 g) were obtained. Those crystals were dissolved under heat in DMF (59 ml). After cooling, ethanol (59 ml) was added. The resulting mixture was seeded, followed by stirring at room temperature for 21 hours. Precipitated crystals were collected, whereby colorless crystals (8.49 g) were obtained. Those crystals were added under stirring to a chilled 1 N aqueous solution of sodium hydroxide, followed by stirring. The reaction mixture was extracted twice with chloroform. The organic layers were combined, washed with saturated brine, dried over anhydrous sodium sulfate, and then concentrated under reduced pressure.

Colorless crystals so obtained were recrystallized twice from 2-propanol, whereby colorless crystals (4.75 g) were obtained (yield: 24%).

Melting point: 168.5–170.0° C.

Specific rotation $[\alpha]_D^{20}$: −7.27 (c=3.00, MeOH)

Those crystals were analyzed by HPLC [column: "CHIRALPAC AD 4.6φ×250 mm" (trademark, product of Daicel Chemical Industries, Ltd.), column temperature: 40° C., mobile phase: hexane/ethanol/methanol/diethylamine= 70/10/20/0.1, flow rate: 0.4 ml/min, detection wavelength: 240 nm]. They were found to have an optical purity of 99% e.e. or higher. Further, from the results of an X-ray crystal structure analysis of the L-(+)-tartrate of this compound, it was confirmed to be (−)-(S)-5-[3-[4-(4-fluorophenyl)piperazin-1-yl]propyl]8-hydroxy-1-methyl-1,4,5,6,7,8-hexahydropyrrolo[3,2-c]azepin-4-one [(−)-(S)-isomer of Compound 11].

Preparation Example 11

Synthesis of 1,3-dimethyl-1,4,5,6,7,8-hexahydropyrrolo[3,2-c]azepine-4,8-dione (Compound 12)

To a suspension of potassium t-butoxide (1.62 g, 14.4 mmole) and 18-crown-6 (317 mg, 1.2 mmole) in THF (20 ml), a suspension of 3-methyl-1,4,5,6,7,8-hexahydropyrrolo[3,2-c]azepine-4,8-dione (2.12 g, 12 mmole) in THF (20 ml) and a solution of methyl iodide (2.55 g, 18 mmole) in THF (5 ml) were successively added dropwise, and the reaction mixture was stirred at room temperature. Twenty-four hours later, a solution of-potassium t-butoxide (0.81 g, 7.2 mmole) and methyl iodide (1.28 g, 9.0 mmole) in DMF (5 ml) was added, and 24 hours later, a solution of potassium t-butoxide (0.81 g, 7.2 mmole) and methyl iodide (1.28 g, 9 mmole) in DMF (5 ml) was added further. The reaction mixture was then stirred at room temperature for 3 hours.

The reaction mixture was concentrated under reduced pressure, followed by the addition of saturated brine to the residue. The resulting mixture was extracted with ethyl acetate (3 times). The organic layers were combined, dried over anhydrous sodium sulfate, and then concentrated under reduced pressure. The residue was purified by chromatography on a silica gel column (eluent: 15%-acetone/methylene chloride) and was then recrystallized from ethyl acetate-hexane, whereby the title compound (0.98 g) was obtained (yield: 43%).

Preparation Example 12

Synthesis of 5-(3-chloropropyl)-1,3-dimethyl-1,4,5,6,7,8-hexahydropyrrolo[3,2-c]azepine-4,8-dione (Compound 13)

Using Compound 12 (0.96 g, 5 mmole), potassium t-butoxide (1.12 g, 10 mmole), 1-bromo-3-chloropropane (3.46 g, 22 mmole) and THF (50 ml), the title compound (676 mg) was obtained in a similar manner as in Preparation Example 6 (yield: 50%).

Preparation Example 13

Synthesis of 5-[3-[4-(4-fluorophenyl)piperazin-1-yl]propyl]-1,3-dimethyl-1,4,5,6,7,8-hexahydropyrrolo[3,2-c]azepine-4,8-dione (Compound 14)

Using Compound 13 (557 mg, 2 mmole), 1-(4-fluorophenyl)piperazine (541 mg, 3 mmole), potassium carbonate (415 mg, 3 mmole), sodium iodide (600 mg, 4 mmole) and acetonitrile (30 ml), the title compound (662 mg) was obtained in a similar manner as in Preparation Example 8 (yield: 80%).

Preparation Example 14

Synthesis of 5-[3-[4-(4-fluorophenyl)piperazin-1-yl]propyl]-8-hydroxy-1,3-dimethyl-1,4,5,6,7,8-hexahydropyrrolo[3,2-c3]azepin-4-one (Compound 15)

Using Compound 14 (600 mg, 1.45 mmole), sodium borohydride (600 mg, 15.9 mmole) and ethanol (20 ml), the title compound (368 mg) was obtained in a similar manner as in Preparation Example 9 (yield: 61%).

EXAMPLE 1

Test in Rat Intermittent Claudication Model

Based on the methods proposed by Angersbach, D. et al. in Int. J. Microcirc. Clin. Exp., 7, 15–30 (1988) and by Loots, W. et al. in Am. J. Physiol. 265, H158–H164 (1993), an intermittent claudication model was designed as will be described next. Firstly, male Wistar rats which ranged in age from 9 to 10 weeks were ligated at right femoral arteries under anesthesia with pentobanbital [40 mg/kg, intraperitoneal administration, "Nembutal Injection" (trademark), product of Dainabot Co., Ltd.] and were fed for 1 week. After fasted overnight, a suspension of (−)-(S)-5-[3-[4-(4-fluorophenyl)piperazin-1-yl]propyl]-8-hydroxy-1-methyl-1,4,5,6,7,8-hexahydropyrrolo[3,2-c]azepin-4-one (test compound a) in a 0.5% aqueous solution of carboxymethylcellulose sodium salt was orally administered at 1, 3 and 10 mg/kg, respectively.

After an elapsed time of 60 minutes since the administration, each rat was subjected to anesthetization with urethan (0.4 mg/kg, intraperitoneal administration, product of Sigma Chemical Co.) and α-chloralose (0.08 mg/kg, intraperitoneal administration, product of NACALAI TESQUE, INC.). To administer collagen into artery, a cannula ["SP-31" (trade name), manufactured by Natsume Seisakusho Co., Ltd.] was inserted through the left carotid artery such that its leading end was located on a proximal side of the branching point of the iliac artery. Thereafter, the rat was held in a prone position, and the skin of the right hind leg was flayed to expose the gastrocnemius-plantaris-sole muscle (GPS muscle). The Achilles tendon was bound and cut off, connected to an isometric tension meter ["CBE-1 10 kg" (trade name), manufactured by MINEBEA Co., Ltd.], and then held in place with a resting tension of about 100 g. Further, the sciatic nerve was exposed and then stimulated by rectangular pulse [10 V, 0.5 Ms, 1 Hz; "Electronic Stimulator SEN-3201" (trade name), manufactured by Nihon Kohden Corporation] through a bipolar electrode ["M2-0550" (trade name), manufactured by M.T Giken Co., Ltd.]. Contraction force produced upon electric stimulation was recorded [amplifier: "AP-620G" (trade name), manufactured by Nihon Kohden Corporation, recorder: "WT-645G" (trade name), manufactured by Nihon Kohden Corporation].

After an elapsed time of about 90 minutes since the administration of the test compound, that is, after an elapsed time of about 5 minutes from the initiation of the electric stimulation in the sciatic nerve, a reduction in contraction force (fatigue) was induced by continuously administering a collagen solution [20 μg/kg/min, "Collagenreagent Form" (trade name), product of Moriya Sangyo Co, Ltd.] for 20 minutes into the abdominal aorta (0.333 ml/20 min). During the measurement of contraction force, the rat was kept warm and the exposed muscle and sciatic nerve were protected from drying with physiological saline. Effects of the test compounds were estimated by measuring the contraction force 20 minutes after collagen infusion. The results are presented in Table 1.

TABLE 1

| Dosage (mg/kg) | Contraction force (g) |
|---|---|
| 1 | 93 ± 17 |
| 3 | 116 ± 15 |
| 10 | 122 ± 10 |
| Control (vehicle was administered) | 61 ± 17 |

From the above results, the compound according to the present invention has demonstrated that its oral administration can strongly inhibit a phenomenon of fatigue by a muscle ischemia which occurs when one takes exercise in a state that obstruction of a large artery and platelet aggregation have been induced, and this compound having both platelet aggregation inhibiting action and vasoconstriction inhibiting action has been found to show excellent drug efficacy as an intermittent claudication therapeutic agent.

EXAMPLE 2

Inhibitory Effect on Canine Platelet Aggregation

Four male beagles which ranged in age from 17 to 19 months were used after fasted overnight. A suspension of (−)-(S)-5-[3-[4-(4-fluorophenyl)piperazin-1-yl]propyl]-8-hydroxy-1-methyl-1,4,5,6,7,8-hexahydropyrrolo[3,2-c] azepin-4-one (test compound a) in a 0.5% aqueous solution of carboxymethylcellulose sodium salt was orally administered at 0.1 mg/kg. Before the administration of the test compound and after elapsed times of 1, 2, 4 and 6 hours from the administration, blood samples were collected from the foreleg veins. The blood was sampled using syringes containing a 1/10 volume of a 3.8% aqueous solution of sodium citrate ["cytorate for ESR Measurement" (trade name), product of The Green Cross Corp.].

Each collected blood sample was centrifuged at room temperature and 190 g for 7 minutes, and the upper layer, platelet-rich plasma (PRP), was collected. The remaining blood was centrifuged at 1,500 g for 10 minutes, and the upper layer, platelet-poor plasma (PPP), was collected. Using collagen [final concentration: 0.03 to 5 $\mu$g/ml, "Collagenreagent Form" (trade name), product of Moriya Sangyo Co., Ltd.] and serotonin (final concentration: 1 $\mu$M, serotonin hydrochloride, product of Sigma Chemical Co.) as a platelet proaggrecant, the platelet aggregating ability was measured by the Born turbidimetry. Specifically, using PPP as a control, a solution of calcium chloride (product of NACALAI TESQUE, INC.) was added to PRP at 37° C. to give a final concentration of 1 mM. After 2 minutes, the proaggrecant was added. Variations in transmittance, which took place in the course of subsequent 10 minutes, were measured using a platelet aggregometer measuring instrument ["PAM-8C" (trade name), manufactured by MEBANCS, INC.], and its maximum value was recorded as a platelet aggregation rate (%). Concerning the setting of the collagen concentrations, the PRPs before the administration of the test compound were used, and minimum concentrations at which platelet aggregation did not occur when collagen alone was added but marked platelet aggregation of 50% or higher was induced by concurrent addition of collagen and serotonin were set for each dog, respectively. As an aggregation inhibition rate, the proportion of an aggregation rate after the administration of the test compound relative to an aggregation rate before the administration of the test compound was shown in percentage. The results are presented in Table 2.

TABLE 2

| Time after administration (hr) | Aggregation inhibition rate (%) |
|---|---|
| 1 | 99.7 ± 0.3 |
| 2 | 99.8 ± 0.2 |
| 4 | 99.3 ± 0.7 |
| 6 | 72.5 ± 16.1 |

From the above results, the compound according to the present invention has been found that, when orally administered, its platelet aggregation inhibiting action lasts for a long time.

EXAMPLE 3

Action Against Vasoconstriction Induced by Supernatant of Aggregated Platelets

After a male Japanese white rabbit was anesthetized by intramuscular administration of ketamine (product of sankyo Company, Limited) at 50 mg/kg, a polyethylene-made catheter ["PE240" (trade name), manufactured by Becton Dickinson Co., Ltd.] was inserted into a carotid artery, and the blood was collected with a tube containing a 1/10 volume of a 3.8% aqueous solution of sodium citrate [NACALAI TESQUE, Inc.]. The blood so collected was centrifuged at 90 g (900 rpm) for 15 minutes ["05PR-22" (trade name), manufactured by Hitachi Koki Co., Ltd.] and platelet-rich plasma (PRP) was collected from the upper layer.

After addition of an equiamount of buffer A (25 mM Tris-HCl, 130 mM NaCl, 1.5 mM EDTA, pH 7.4), to PRP, the mixture was centrifuged at 4° C. and 1,500 g (3,000 rpm) for 10 minutes. The thus-obtained platelet pellet was suspended again in buffer A, followed by centrifugation at 4° C. and 1,500 g (3,000 rpm) for 5 minutes. The resulting platelet pellet was suspended again in buffer B (25 mM Tris-HCl, 130 mM NaCl, 0.3 mM EDTA, pH 7.4), followed by centrifugation under the same conditions. The thus-obtained platelet pellet was finally suspended in buffer C (25 mM Tris-HCl, 130 mM NaCl, 0.1% glucose, 0.1% BSA, pH 7.4) (at a rate of 1 ml of buffer C to 4 ml of PRP), whereby a washed platelet suspension was prepared.

To the thus-obtained washed platelet suspension, 1 mM $CaCl_2$ (product of NACALAI TESQUE, INC.) and 0.2 U/ml thrombin (product of Mochida Pharmaceutical Co., Ltd.) were added. The resulting mixture was shaken at 37° C. for 5 minutes, whereby platelet aggregation was induced. The mixture was then centrifuged at 4° C. and 1,500 g (3,000 rpm) for 10 minutes so that the aggregate was caused to precipitate. The supernatant was used as an aggregated platelet supernatant in experiments.

On the other hand, various blood vessels (coronary arteries, basilar arteries, mesenteric arteries, renal arteries and femoral arteries) were excised from the rabbit from which the blood had been collected. Under a stereoscopic microscope, helical strip preparations (length: about 20 mm, width: 1 to 2 mm) were prepared. In Magnus cylinders (7 ml) filled with Tyrode solution (5.4 mM KCl, 136.9 mM NaCl, 2.7 mM $CaCl_2.2H_2O$, 0.5 mM $MgCl_2.6H_2O$, 11.9 mM $NaHCO_3$, 0.45 mM $NaH_2PO_4.2H_2O$, 5.5 mM glucose) which had been saturated with 95% $O_2$+5% $CO_2$ mixed gas and was heated at 37° C., the vascular strip preparations were separately suspended under a load of 0.5 g, with upper end portions thereof being connected via silk threads to isometric transducers ["UL-10GR" (trade name), manufactured by MINEBEA Co., Ltd. or "TB-612T" (trade name), manufactured by Nihon Kohden Corporation], respectively.

After the vascular strip preparations had been left over for about 1 hour and their resting tensions had been confirmed to become stable, the tonicities of the vascular strip preparations were measured using the isometric transducers. With respect to each vascular strip preparation, subsequent to confirmation of a contractive response by the addition of 30 mM KCl (product of NACALAI TESQUE, INC.), the vascular strip preparation was washed with Tyrode solution to have its tonicity returned to the previous level. After the vascular strip preparations were left over for 30 minutes or longer and were allowed to become stable, the aggregated platelet supernatant (1/100-fold dilution) was added. After confirming the induction of tonic contractions, (−)-(S)-5-[3-[4-(4-fluorophenyl)piperazin-1-yl]propyl]-8-hydroxy-1- methyl-1,4,5,6,7,8-hexahydropyrrolo[3,2-c]azepin-4-one (test compound a) was added at 1 to 1,000 nM to the individual Magnus cylinders to study its relaxing action against the contractive responses. Assuming that the contraction rates before the addition of the compound be 100%, concentrations effective to develop 50% relaxation ($EC_{50}$) were determined. The results are presented in Table 3.

TABLE 3

| Blood vessel | $EC_{50}$ (nM) |
|---|---|
| Coronary artery | 254 ± 54 |
| Basilar artery | 138 ± 55 |
| Pulmonary artery | 14 ± 3 |
| Mesenteric artery | 32 ± 22 |
| Renal artery | 246 ± 79 |
| Femoral artery | 328 ± 112 |

From the above results, the compound according to the present invention has been found to inhibit vasoconstriction caused by an aggregated platelet supernatant.

EXAMPLE 4

Inhibitory Action in Mouse Pulmonary Thromboembolic Death

Male ddY mice which ranged in age from 4 to 5 weeks were used after fasted overnight. Suspensions of Compounds a–c, which will be specified subsequently herein, in a 0.5% aqueous solution of carboxymethylcellulose sodium were orally administered at 3 mg/kg.

After 1 hour, collagen [1 mg/kg, "Collagenreagent Form" (trade name), product of Moriya Sangyo Co., Ltd.] and serotonin hydrochloride (5 mg/kg, product of Sigma Chemical Co.) were injected through the candal veins.

An investigation was made for mortality rates of mice within 10 minutes after the injection. The results are presented in Table 4.

(Test Compounds)

Compound a:
(−)-(S)-5-[3-[4-(4-fluorophenyl)piperazin-1-yl)propyl]-8-hydroxy-1-methyl-1,4,5,6,7,8-hexahydropyrrolo[3,2-c]azepin-4-one Compound b:
(±)-5-[3-[4-(4-fluorophenyl)piperazin-1-yl]propyl]-8-hydroxy-1-methyl-1,4,5,6,7,8-hexahydropyrrolo[3,2-c]azepin-4-one Compound c:
5-[3-[4-(4-fluorophenyl)piperazin-1-yl]propyl]-8-hydroxy-1,3-dimethyl-1,4,5,6,7,8-hexahydropyrrolo[3,2-c]azepin-4-one

TABLE 4

| Compound | Mortality rate (%) | Number of mice |
|---|---|---|
| a | 10 | 10 |
| b | 25 | 20 |
| c | 30 | 10 |
| Control (vehicle was administered) | 88 | 50 |

From the above results, the compounds according to the present invention have been found to strongly inhibit pulmonary thromboembolic death caused by platelet aggregation when administered orally.

EXAMPLE 5

Toxicity Test in Mouse

A suspension of (−)-(S)-5-(3-[4-(4-fluorophenyl)piperazin-1-yl]propyl]-8-hydroxy-1-methyl-1,4,5,6,7,8-hexahydropyrrolo[3,2-c]azepin-4-one (test compound a) in a 1% aqueous solution of hydroxypropylcellulose was orally administered at 300 mg/kg to 6 male ICR mice which ranged in age from 8 to 9 weeks. No case of death was observed.

INDUSTRIAL APPLICABILITY

The intermittent claudication therapeutic drug, which comprises the pyrroloazepine of the formula (I) or a pharmacologically acceptable salt thereof as an active ingredient, can be administered to patients complaining intermittent claudication or to patients who are likely to develop intermittent claudication. Illustrative of the patients, who are complaining intermittent claudication, are patients with peripheral circulatory disturbances and patients suffering from chronic arterial occlusive diseases, for example, arteriosclerosis obliterans or thromboangiitis obliterans. The intermittent claudication therapeutic drug can be used to prevent or treat such diseases.

What is claimed is:

1. A method of treating or improving intermittent claudication, which comprises administering, to a patient with intermittent claudication, a pyrroloazepine derivative or a pharmacologically acceptable salt thereof, said pyrroloazepine derivative being represented by the following formula (I):

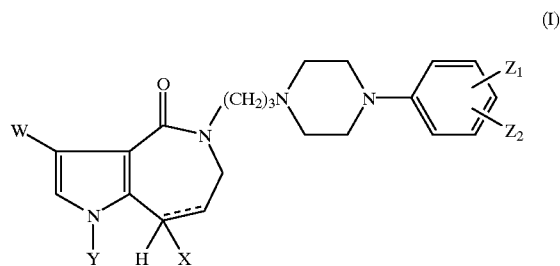

wherein the dotted line indicates existence or non-existence of a bond; when the bond of the dotted line exists, X does not exist, and, when the bond of the dotted line does not exist, X represents a hydrogen atom, a hydroxy group or a group $OR_1$ in which $R_1$ represents a substituted or unsubstituted alkyl group; Y represents a linear or branched, substituted or unsubstituted alkyl group; $Z_1$ and $Z_2$ are the same or different and each independently represent a hydrogen atom, a hydroxy group or a halogen atom; and W represents a hydrogen atom or a methyl group.

2. The method of claim 1, wherein said pyrroloazepine derivative (I) or said pharmacologically acceptable salt thereof is orally administered.

3. The method of claim 1 wherein said pyrroloazepine derivative is represented by the formula (I) in which the bond of the dotted line does not exist, W is a hydrogen atom, and X is a hydroxy group.

4. The method according to claim 1 wherein said pyrroloazepine derivative is represented by the formula (I) in which the bond of the dotted line does not exist, W is a hydrogen atom, X is a hydroxy group, $Z_1$ is a hydrogen atom, and $Z_2$ is a halogen atom.

5. The method according to claim 1 wherein said pyrroloazepine derivative is (±)-5-[3-[4-(4-fluorophenyl)piperazin-1-yl]propyl]-8-hydroxy-1-methyl-1,4,5,6,7,8- hexahydropyrrolo[3,2-c]azepin4-one or a pharmacologically acceptable salt thereof.

6. The method according to claim 1 wherein said pyrroloazepine derivative is (−)-(S)-5-[3-[4-(4-fluorophenyl)piperazin-1-yl]propyl]-8-hydroxy-1-methyl-1,4,5,6,7,8-hexahydropyrrolo[3,2-c]azepin4-one or a pharmacologically acceptable salt thereof.

* * * * *